(12) United States Patent
Roth

(10) Patent No.: US 8,733,356 B1
(45) Date of Patent: May 27, 2014

(54) GERMICIDAL PROTECTIVE MASK WITH ULTRAVIOLET LIGHT EMITTING DIODES

(76) Inventor: Jon N. Roth, Palm Harbor, FL (US)

( * ) Notice: Subject to any disclaimer, the term of this patent is extended or adjusted under 35 U.S.C. 154(b) by 858 days.

(21) Appl. No.: 12/658,215

(22) Filed: Feb. 4, 2010

(51) Int. Cl.
*A62B 7/10* (2006.01)
*A62B 23/02* (2006.01)

(52) U.S. Cl.
USPC .................................. 128/205.27; 128/206.12

(58) Field of Classification Search
USPC .................. 128/200.28, 205.27, 909, 201.25, 128/205.12; 362/103
See application file for complete search history.

(56) References Cited

U.S. PATENT DOCUMENTS

| | | | |
|---|---|---|---|
| 5,165,395 A * | 11/1992 | Ricci | 128/205.27 |
| 6,523,179 B1 * | 2/2003 | Zegarelli et al. | 2/9 |
| 6,595,207 B1 | 7/2003 | McDonald | |
| 6,691,706 B2 | 2/2004 | Ives | |
| 6,901,930 B2 * | 6/2005 | Henley | 128/205.27 |
| 7,523,750 B2 | 4/2009 | Krzysztofik | |
| 8,001,968 B2 * | 8/2011 | Doty et al. | 128/205.27 |
| 2004/0216745 A1 * | 11/2004 | Yuen et al. | 128/205.27 |
| 2008/0232092 A1 | 9/2008 | Carter | |

* cited by examiner

*Primary Examiner* — Nicholas Lucchesi
*Assistant Examiner* — Jenna Zhang

(57) ABSTRACT

A support has an interior section positionable on one side of a wearer's head. The support has an exterior section positionable over the wearer's face. The exterior section has a free end with a recess. A plurality of light emitters is located in the recess and adapted to function within the germicidal spectrum for air. An electrical assembly is coupled to the light emitters. A shield of light is formed adjacent to the wearer's nose and mouth. When the wearer breathes air, the breathed air becomes sanitized by the passage of pathogens through a curtain of light immediately prior to being breathed.

14 Claims, 4 Drawing Sheets

GERMICIDAL PROTECTIVE MASK WITH ULTRAVIOLET LIGHT EMITTING DIODES

BACKGROUND OF THE INVENTION

1. Field of the Invention

The present invention relates to a germicidal protective mask ultraviolet light emitting diodes and more particularly pertains to sanitizing air immediately prior to being breathed by a wearer, the sanitizing being done in a safe, reliable, efficient and economical manner.

2. Description of the Prior Art

The use of protective masks of known designs and configurations is known in the prior art. More specifically, protective masks of known designs and configurations previously devised and utilized for the purpose of sanitizing air before being breathed by a wearer through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 6,595,207 issued Jul. 22, 2003 to McDonald relates to an Oxygen Diffuser for Patient Oxygen Delivery System. U.S. Pat. No. 6,691,706 issued Feb. 17, 2004 to Ives relates to a Personal Humidifier. U.S. Pat. No. 7,523,750 issued Apr. 28, 2009 relates to a Breathing Respirator. Lastly, U.S. Patent Application Publication Number 2008/0232092 published Sep. 25, 2008 to Carter relates to a LED Cap Light.

While these devices fulfill their respective, particular objectives and requirements, the aforementioned patents do not describe a germicidal protective mask ultraviolet light emitting diodes that allows for sanitizing air immediately prior to being breathed by a wearer, the sanitizing being done in a safe, reliable, efficient and economical manner.

In this respect, the germicidal protective mask ultraviolet light emitting diodes according to the present invention substantially departs from the conventional concepts and designs of the prior art, and in doing so provides an apparatus primarily developed for the purpose of sanitizing air immediately prior to being breathed by a wearer, the sanitizing being done in a safe, reliable, efficient and economical manner.

Therefore, it can be appreciated that there exists a continuing need for a new and improved germicidal protective mask ultraviolet light emitting diodes which can be used for sanitizing air immediately prior to being breathed by a wearer, the sanitizing being done in a safe, reliable, efficient and economical manner. In this regard, the present invention substantially fulfills this need.

SUMMARY OF THE INVENTION

In view of the foregoing disadvantages inherent in the known types of protective masks of known designs and configurations now present in the prior art, the present invention provides an improved germicidal protective mask ultraviolet light emitting diodes. As such, the general purpose of the present invention, which will be described subsequently in greater detail, is to provide a new and improved germicidal protective mask ultraviolet light emitting diodes and method which has all the advantages of the prior art and none of the disadvantages.

To attain this, the present invention essentially comprises a germicidal protective mask ultraviolet light emitting diodes. First provided is a support. The support has an interior section. The interior section is positionable on one side of a wearer's head. The support has an exterior section. The exterior section extends from the interior section. The exterior section is positionable over the wearer's face. The exterior section has a forked free end. The exterior section has an upper horizontal leg and a parallel lower leg. The legs are spaced. In this manner a passageway is formed for the flow of air into the wearer's mouth. A downwardly facing recess is formed in the upper leg. An upwardly facing recess is formed in the lower leg.

A linear adjustment mechanism is provided. The linear adjustment mechanism couples the interior and exterior sections. The linear adjustment mechanism includes a linear passageway. The linear passageway is formed in the exterior section. A linear projection is formed in the interior section. The linear projection is slidably received in the linear passageway. A plurality of linearly aligned holes is formed in the linear passageway. A ball is provided. The ball is resiliently supported in the linear projection. The ball is selectively received within one of the holes. In this manner the length of the support may be varied.

Provided next is an inverted hook. The hook has a lower end. The hook has an upper end. The hook has a central extent. The hook is positionable over an ear of the wearer.

A rotary adjustment mechanism is provided next. The rotary adjustment mechanism couples the hook and the interior section. The rotary adjustment mechanism includes a first circular face. The first circular face is formed on the upper end of the hook. The rotary adjustment mechanism includes a second circular face. The second circular face is formed on the interior section of the support remote from the linear coupling mechanism. The rotary adjustment mechanism includes a pivot pin. The pivot pin rotatably supports the first and second circular faces.

Further provided is a plurality of ultraviolet light emitting diodes. The light emitting diodes are located in the upwardly and downwardly facing recesses of the legs.

Provided last is an electrical assembly. The electrical assembly includes a housing. The housing has batteries. The housing has an on/off switch. The electrical assembly includes electrical lines. The electrical lines extend from the batteries through the hook and the support to the light emitting diodes. The light emitting diodes, when energized, are adapted to form a shield of ultraviolet light over the wearer's nose and mouth. In this manner when the wearer breathes air, the breathed air will become sanitized by passage of pathogens through a curtain of ultraviolet light immediately prior to being breathed, the first circular face having first electrical contacts and the second circular face having second electrical contacts, the electrical contacts allowing the flow of current to the light emitting diodes when positioned over the wearer's mouth and nose. The electrical contacts terminate the flow of current to the light emitting diodes when pivoted away from the wearer's mouth and nose.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved germicidal protective mask ultraviolet light emitting diodes which has all of the advantages of the prior art protective masks of known designs and configurations and none of the disadvantages.

It is another object of the present invention to provide a new and improved germicidal protective mask ultraviolet light emitting diodes which may be easily and efficiently manufactured and marketed.

It is a further object of the present invention to provide a new and improved germicidal protective mask ultraviolet light emitting diodes which is of durable and reliable constructions.

An even further object of the present invention is to provide a new and improved germicidal protective mask ultraviolet light emitting diodes which is susceptible of a low cost of manufacture with regard to both materials and labor, and which accordingly is then susceptible of low prices of sale to the consuming public, thereby making such germicidal protective mask ultraviolet light emitting diodes economically available to the buying public.

Even still another object of the present invention is to provide a germicidal protective mask ultraviolet light emitting diodes for sanitizing air immediately prior to being breathed by a wearer, the sanitizing being done in a safe, reliable, efficient and economical manner.

Lastly, it is an object of the present invention to provide a new and improved germicidal protective mask light emitters. A support has an interior section positionable on one side of a wearer's head. The support has an exterior section positionable over the wearer's face. The exterior section has a free end with a recess. A plurality of light emitters is located in the recess and adapted to function within the germicidal spectrum for air. An electrical assembly is coupled to the light emitters. A shield of light is formed adjacent to the wearer's nose and mouth. When the wearer breathes air, the breathed air becomes sanitized by the passage of pathogens through a curtain of light immediately prior to being breathed.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
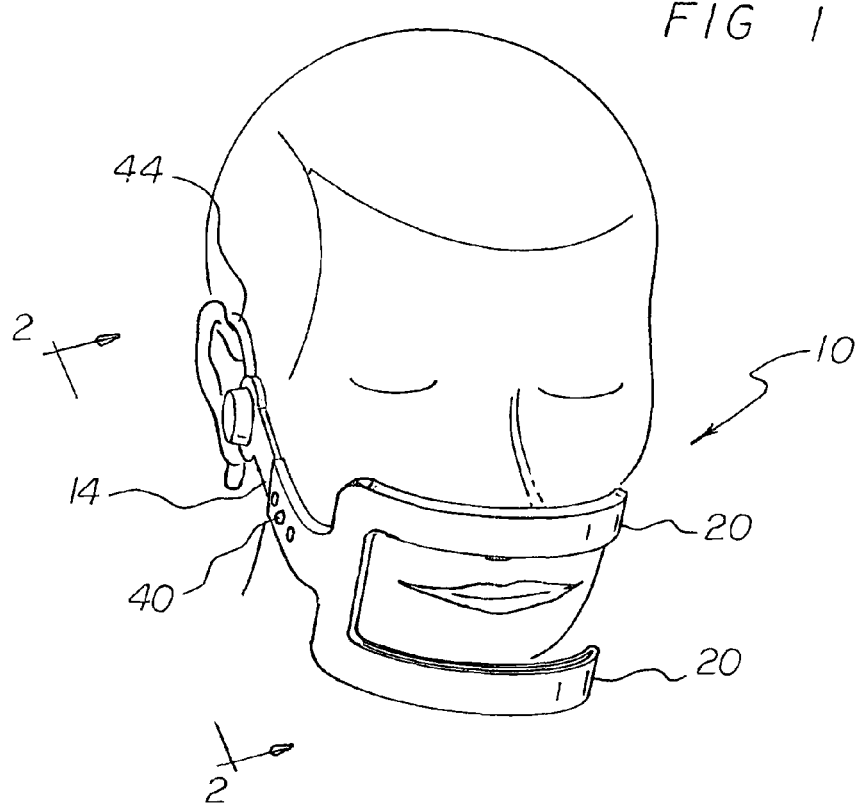
FIG. 1 is a perspective illustration of a germicidal protective mask ultraviolet light emitting diodes with ultraviolet light emitting diodes system constructed in accordance with the principles of the present invention.
Figure 2:
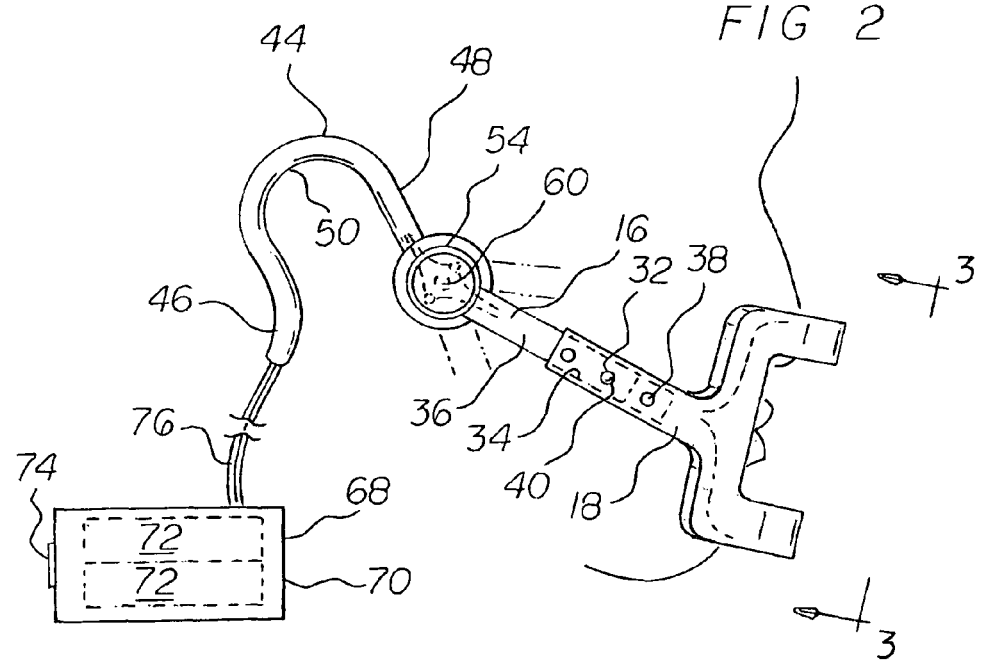
FIG. 2 is a side elevational view of the system taken along line 2-2 of FIG. 1.
Figure 3:
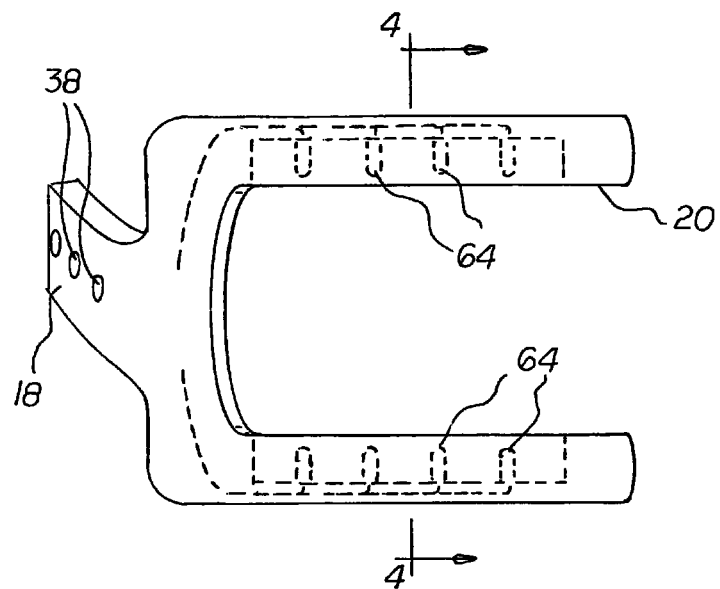
FIG. 3 is a front elevational view taken along line 3-3 of FIG. 2.
Figure 4:
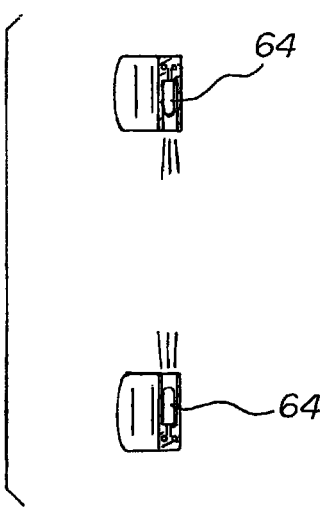
FIG. 4 is a cross sectional view taken along line 4-4 of FIG. 3.
Figure 5:
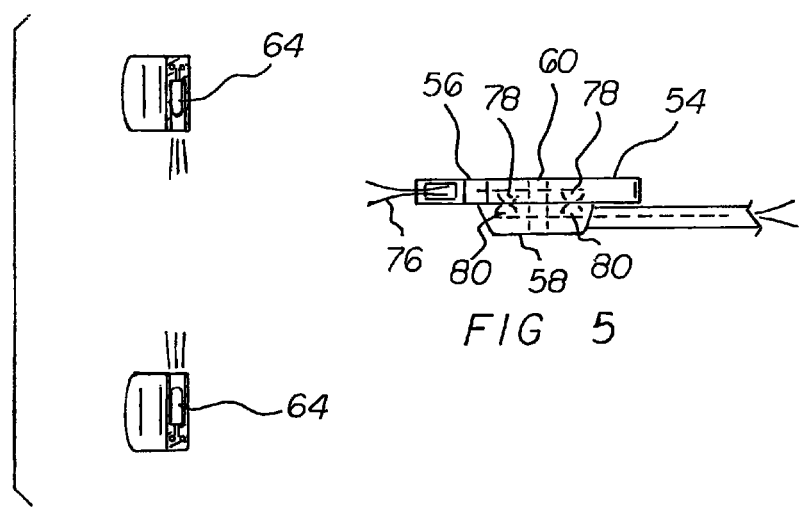
FIG. 5 is a plan view taken along line 5-5 of FIG. 2.

With reference now to the drawings, and in particular to FIG. 1 thereof, the preferred embodiment of the new and improved germicidal protective mask ultraviolet light emitting diodes embodying the principles and concepts of the present invention and generally designated by the reference numeral 10 will be described.

The present invention, the germicidal protective mask ultraviolet light emitting diodes (10) is comprised of a plurality of components. Such components in their broadest context include a support, a plurality of ultraviolet light emitting diodes, and an electrical assembly. Such components are individually configured and correlated with respect to each other so as to attain the desired objective.

First provided is a support (14). The support has an interior section (16). The interior section is positionable on one side of a wearer's head. The support has an exterior section (18). The exterior section extends from the interior section. The exterior section is positionable over the wearer's face. The exterior section has a forked free end (20). The exterior section has an upper horizontal leg and a parallel lower leg. The legs are spaced. In this manner a passageway is formed for the flow of air into the wearer's mouth. A downwardly facing recess is formed in the upper leg. An upwardly facing recess is formed in the lower leg.

A linear adjustment mechanism (32) is provided. The linear adjustment mechanism couples the interior and exterior sections. The linear adjustment mechanism includes a linear passageway (34). The linear passageway is formed in the exterior section. A linear projection (36) us formed in the interior section. The linear projection is slidably received in the linear passageway. A plurality of linearly aligned holes (38) is formed in the linear passageway. A ball (40) is provided. The ball is resiliently supported in the linear projection. The ball is selectively received within one of the holes. In this manner the length of the support may be varied.

Provided next is an inverted hook (44). The hook has a lower end (46). The hook has an upper end (48). The hook has a central extent (50). The hook is positionable over an ear of the wearer.

A rotary adjustment mechanism (54) is provided next. The rotary adjustment mechanism couples the hook and the interior section. The rotary adjustment mechanism includes a first circular face (56). The first circular face is formed on the upper end of the hook. The rotary adjustment mechanism includes a second circular face (58). The second circular face is formed on the interior section (16) of the support (14) remote from the linear coupling mechanism. The rotary adjustment mechanism includes a pivot pin (60). The pivot pin rotatably supports the first and second circular faces.

Further provided is a plurality of ultraviolet light emitting diodes (64). The light emitting diodes are located in the upwardly and downwardly facing recesses of the legs.

Provided last is an electrical assembly (68). The electrical assembly includes a housing (70). The housing has batteries (72). The housing has an on/off switch (74). The electrical assembly includes electrical lines (76). The electrical lines extend from the batteries through the hook (44) and the support (14) to the light emitting diodes. The light emitting diodes, when energized, are adapted to form a shield of ultraviolet light over the wearer's nose and mouth. In this manner when the wearer breathes air, the breathed air will become sanitized by passage of pathogens through a curtain of ultraviolet light immediately prior to being breathed, the first circular face having first electrical contacts (78) and the second circular face having second electrical contacts (80), the electrical contacts allowing the flow of current to the light emitting diodes when positioned over the wearer's mouth and nose. The electrical contacts terminate the flow of current to the light emitting diodes when pivoted away from the wearer's mouth and nose.

Figure 6:
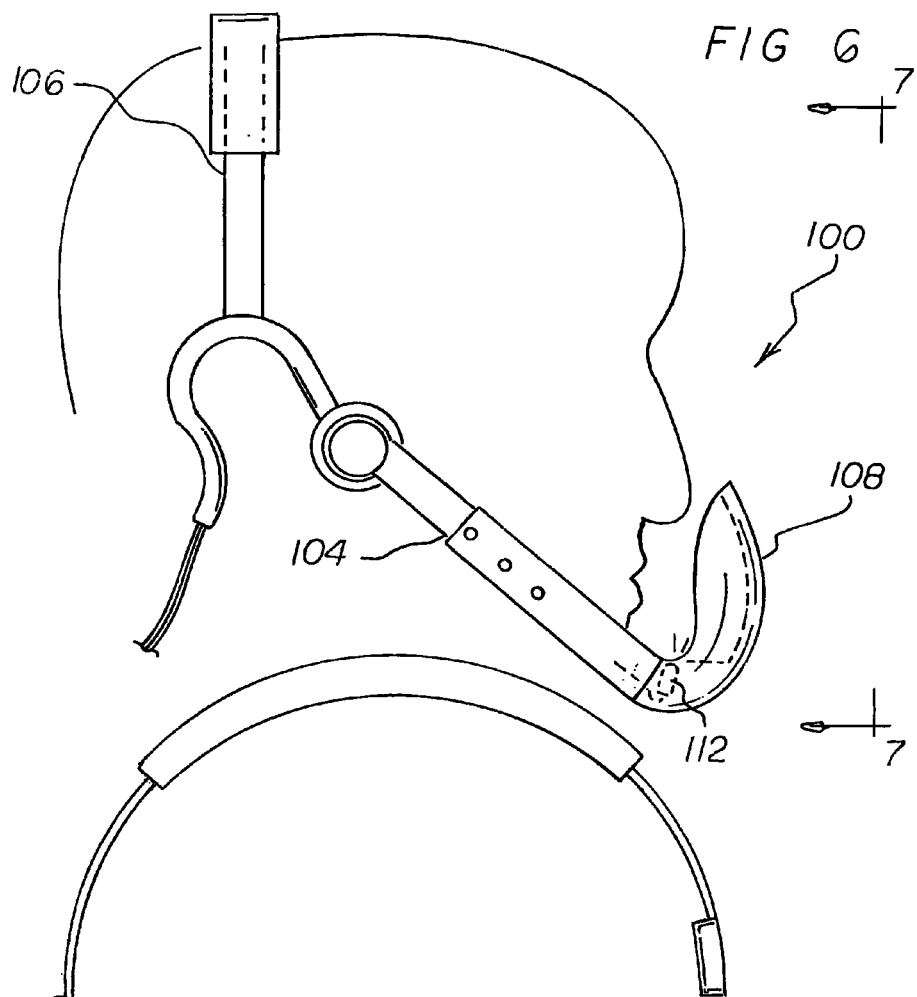
FIG. 6 is a side elevational view of an alternate embodiment of the invention.
Figure 7:
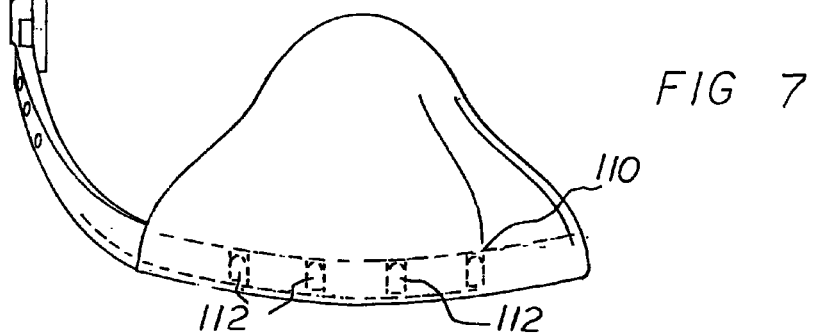
FIG. 7 is a front elevational view taken along line 7-7 of FIG. 6.

Reference is now made to the alternate embodiment (100) of the invention illustrated in FIGS. 6 and 7. In this embodiment, the support (104) includes a resilient strap (106). The resilient strap is positioned over the wearer's head. The free end of the exterior section is shaped as a shield (108) positionable over the wearer's mouth and nose. The shield has an upwardly facing recess (110) supporting the light emitting diodes (112) beneath the wearer's mouth.

Figure 8:
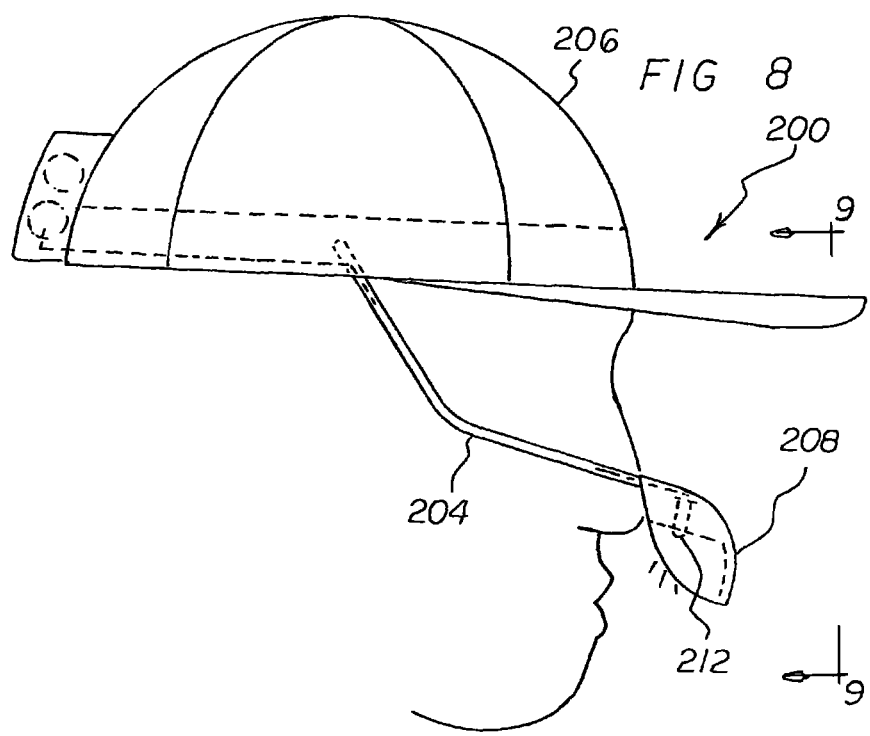
FIG. 8 is a side elevational view of a final alternate embodiment of the invention.
Figure 9:
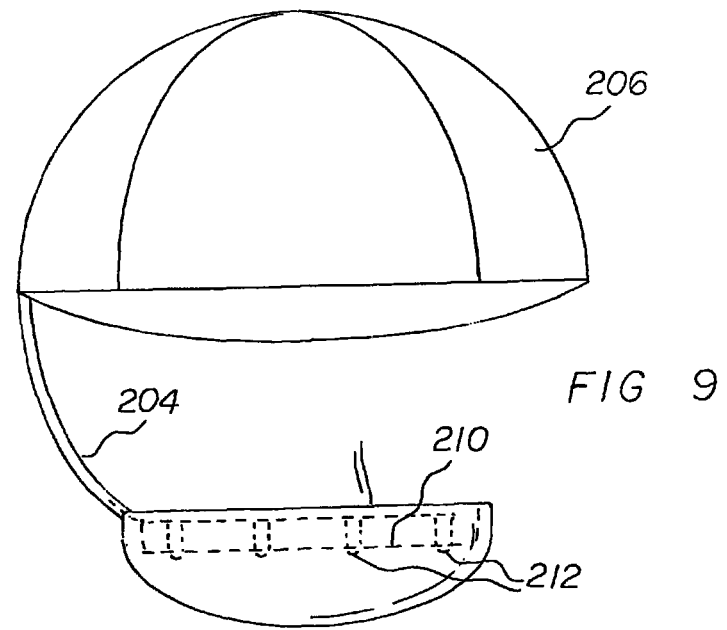
FIG. 9 is a front elevational view taken along line 9-9 of FIG. 8.

Reference is now made to the alternate embodiment (200) of the invention illustrated in FIGS. 8 and 9. In this embodiment, the support (204) includes a cap (206). The cap is positioned on the wearer's head. The free end of the exterior section is shaped as a shield (208). The shield is positionable over the wearer's mouth and nose. The shield has a downwardly facing recess (210) supporting the light emitting diodes (212) above the wearer's nose.

In the preferred embodiment, the light emitters are light emitting diodes and the curtain of light is ultraviolet light (UVC). The preferred wavelength for the light is commonly centered around 253.7 nm with a window of 240 to 270 nm to be effective on the airborne germicidal irradiation curve. In a final alternate embodiment of the invention, the light emitting diodes are replaced with mercury vapor pressure lamps for the same ultraviolet effect.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A protective mask adapted to emit light comprising:
    a support having an interior section positionable on one side of a wearer's nose and mouth and an exterior section positionable over the wearer's nose and mouth, the exterior section having a free end with a recess;
    a plurality of light emitters located in the recess and adapted to function within the germicidal spectrum for air; and
    an electrical assembly coupled to the light emitters to form a shield curtain of light adjacent to the wearer's nose and mouth for the passage of unfiltered ambient air through the curtain of light into the wearer's nose and mouth whereby when the wearer breathes air, the breathed air will become sanitized by the passage of pathogens through the curtain of light immediately prior to being breathed;
    wherein the free end of the exterior section is fork shaped with an upper horizontal leg and a parallel lower leg, the legs being separated to form a space constituting a passageway for the flow of air into the wearer's mouth, a downwardly facing recess formed in the upper leg and an upwardly facing recess formed in the lower leg, the recesses supporting the light emitters.

2. The mask as set forth in claim 1 wherein the light emitters are light emitting diodes.

3. The mask as set forth in claim 1 wherein the curtain of light is ultraviolet light.

4. The mask as set forth in claim 1 wherein the light emitters are mercury vapor pressure lamps.

5. The mask as set forth in claim 1 and further including a hook operatively coupled to the support and removably positionable over an ear of the wearer.

6. The mask as set forth in claim 1 and further including a linear adjustment mechanism for varying the length of the support.

7. The mask as set forth in claim 1 and further including a rotary adjustment mechanism for varying the angular orientation of the support.

8. The mask as set forth in claim 7 wherein the rotary adjustment mechanism includes a first circular face having first electrical contacts and a second circular face having second electrical contacts, the first electrical contacts and the second electrical contacts allowing the flow of current to the light emitters when positioned over the wearer's mouth and nose, the first electrical contacts and the second electrical contacts terminating the flow of current to the light emitters when pivoted away from the wearer's mouth and nose.

9. The mask (100) as set forth in claim 1 wherein the support (104) includes a resilient strap (106) positioned over the wearer's head.

10. The mask as set forth in claim 1 wherein the free end of the exterior section is shaped as a shield (108) positionable over the wearer's mouth and nose, the shield having an upwardly facing recess (110) supporting the light emitters (112) beneath the wearer's mouth.

11. The mask (200) as set forth in claim 1 wherein the support (204) includes a cap (206) positioned on the wearer's head.

12. The mask as set forth in claim 1 wherein the free end of the exterior section is shaped as a shield (208) positionable over the wearer's mouth nose, the shield having a downwardly facing recess (210) supporting the light emitters (212) above the wearer's nose.

13. A germicidal protective mask ultraviolet light emitting diodes (10) with ultraviolet light emitting diodes for sanitizing air immediately prior to being breathed by a wearer, the system comprising, in combination:

a support (14) having an interior section (16) positionable on one side of a wearer's head and an exterior section (18) extending from the interior section and positionable over the wearer's face, the exterior section having a forked free end (20) with an upper horizontal leg and a parallel lower leg, the legs being spaced to form a passageway for the flow of air into the wearer's mouth, a downwardly facing recess formed in the upper leg and an upwardly facing recess formed in the lower leg, a linear adjustment mechanism (32) coupling the interior and exterior sections, the linear adjustment mechanism including a linear passageway (34) formed in the exterior section and a linear projection (36) formed in the interior section, the linear projection being slidably received in the linear passageway, a plurality of linearly aligned holes (38) formed in the linear passageway and a ball (40) resiliently supported in the linear projection, the ball being selectively received within one of the holes to vary the length of the support;

an inverted hook (44) formed with a lower end (46) and an upper end (48) and a central extent (50) positionable over an ear of the wearer;

a rotary adjustment mechanism (54) coupling the hook and the interior section, the rotary adjustment mechanism including a first circular face (56) formed on the upper end of the hook, the rotary adjustment mechanism including a second circular face (58) formed on the interior section (16) of the support (14) remote from the linear coupling mechanism, a pivot pin (60) rotatably supporting the first and second circular faces;

a plurality of ultraviolet light emitting diodes (64) located in the upwardly and downwardly facing recesses of the legs and adapted to function within the germicidal spectrum for air; and an electrical assembly (68) including a housing (70) with batteries (72) and an on/off switch (74), electrical lines (76) extending from the batteries through the hook (44) and the support (14) to the light emitting diodes, the light emitting diodes when energized adapted to form a curtain of ultraviolet light over the wearer's nose and mouth whereby when the wearer breathes air, the breathed air will become sanitized by passage of pathogens through a curtain of ultraviolet light immediately prior to being breathed, the first circular face having first electrical contacts (78) and the second circular face having second electrical contacts (80), the first electrical contacts and the second electrical contacts allowing the flow of current to the light emitting diodes when positioned over the wearer's mouth and nose, the first electrical contacts and the second electrical contacts terminating the flow of current to the light emitting diodes when pivoted away from the wearer's mouth and nose.

14. A germicidal protective mask (10) with ultraviolet light emitting diodes for sanitizing air immediately prior to being breathed by a wearer, the system comprising, in combination:

a support (14) having an interior section (16) positionable on one side of a wearer's head and an exterior section (18) extending from the interior section and positionable over a wearer's face, the exterior section having a forked free end (20) with an upper horizontal leg and a parallel lower leg, the legs being spaced to form a passageway for the flow of unfiltered air into the wearer's mouth, a downwardly facing recess formed in the upper leg and an upwardly facing recess formed in the lower leg, a plurality of ultraviolet light emitting diodes (64) located in the upwardly facing recess and the downwardly facing recess of the legs and adapted to function within the germicidal spectrum for air; and an electrical assembly (68) including a housing (70) with batteries (72) and an on/off switch (74) and electrical lines (76) extending from the batteries to the light emitting diodes, the light emitting diodes when energized adapted to form a curtain of ultraviolet light over the wearer's nose and mouth whereby when the wearer breathes air, the breathed air will become sanitized by passage of pathogens through a curtain of ultraviolet light immediately prior to being breathed.

* * * * *